United States Patent [19]

Falk et al.

[11] Patent Number: 5,591,894

[45] Date of Patent: Jan. 7, 1997

[54] HYDROGEN SAMPLER FOR MOLTEN METAL AND METHOD

[75] Inventors: Richard A. Falk, Hillsboro Beach, Fla.; Robert W. Nott, Ontario, Canada

[73] Assignee: Midwest Instrument Co., Inc., Hartland, Wis.

[21] Appl. No.: 543,396

[22] Filed: Oct. 16, 1995

Related U.S. Application Data

[63] Continuation-in-part of Ser. No. 500,318, Jul. 10, 1995, abandoned.

[51] Int. Cl.⁶ .................................................. G01N 7/00
[52] U.S. Cl. .................. 73/19.07; 73/864.34; 73/864.73
[58] Field of Search ........................... 73/19.07, DIG. 9, 73/864.34, 864.81, 864.73

[56] References Cited

U.S. PATENT DOCUMENTS

| | | |
|---|---|---|
| 2,861,450 | 11/1958 | Ransley . |
| 3,820,380 | 6/1974 | Miller et al. ............................ 73/19.07 |
| 4,331,023 | 5/1982 | Allersma et al. ....................... 73/19.07 |
| 4,453,424 | 6/1984 | Hackett ................................. 73/864.58 |
| 4,454,748 | 6/1984 | Terai et al. . |
| 4,624,128 | 11/1986 | Pelton . |
| 4,731,732 | 3/1988 | Warchol et al. . |
| 4,757,707 | 7/1988 | Harvey et al. . |
| 4,878,375 | 11/1989 | Roggen ................................. 73/19.07 |
| 4,907,440 | 3/1990 | Martin et al. . |
| 4,918,974 | 4/1990 | Hachey et al. . |
| 4,998,432 | 3/1991 | Plessers et al. . |
| 5,345,808 | 9/1994 | Sigworth ............................... 73/19.07 |

Primary Examiner—Robert Raevis
Attorney, Agent, or Firm—Ryan, Maki, Mann & Hohenfeldt

[57] ABSTRACT

An immersion probe for determination of the concentration of a gas dissolved in molten metal includes a probe body in the form of an elongated hermetically sealed housing. The body has a first end adapted to be connected to a gas inlet and a gas outlet, which first end may be hermetically sealed by a temporary sealing means. The body has a second end adapted to be immersed in molten metal, the second end is spaced from and in fluid flow communication with the first end and has a gas-permeable, liquid metal-impervious plug. The second end and the plug are hermetically sealed by a molten metal-soluble cap until melted during immersion into molten metal. An inert, dry carrier gas such as nitrogen or argon may be sealed within the probe body. A metal sleeve around the probe body, preferably of a composition fusible in and compatible with a molten metal being monitored may be used to provide a gas impermeable seal for the probe body. After a short cycle of purging with an inert gas after immersion, a vacuum is drawn and a gas concentration is determined by an analysis device.

35 Claims, 4 Drawing Sheets

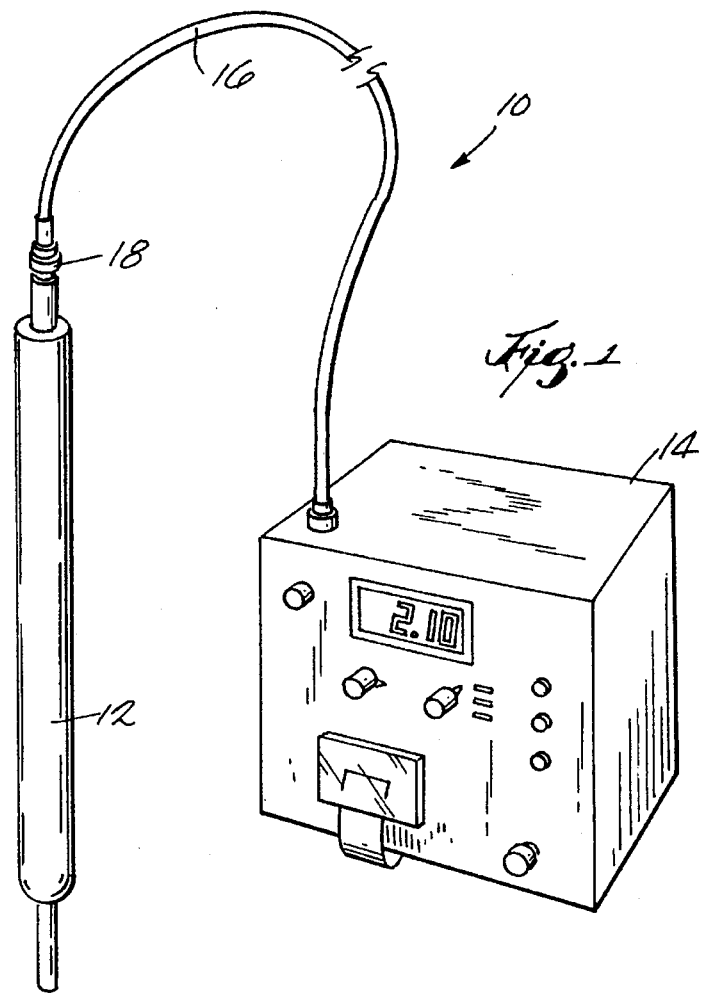
Fig. 1
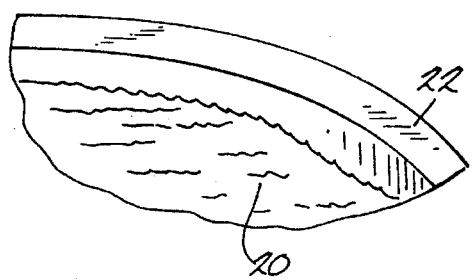
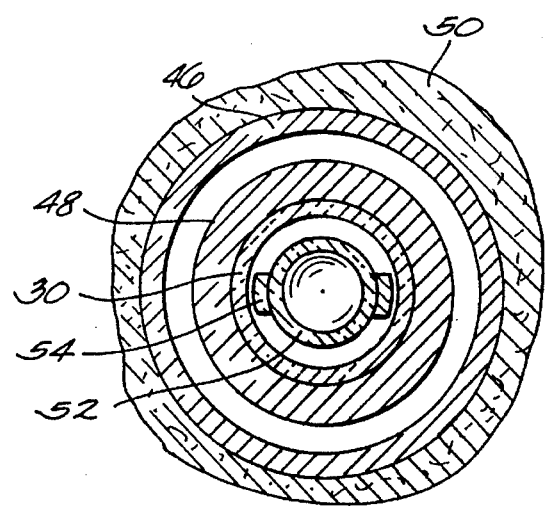
Fig. 3

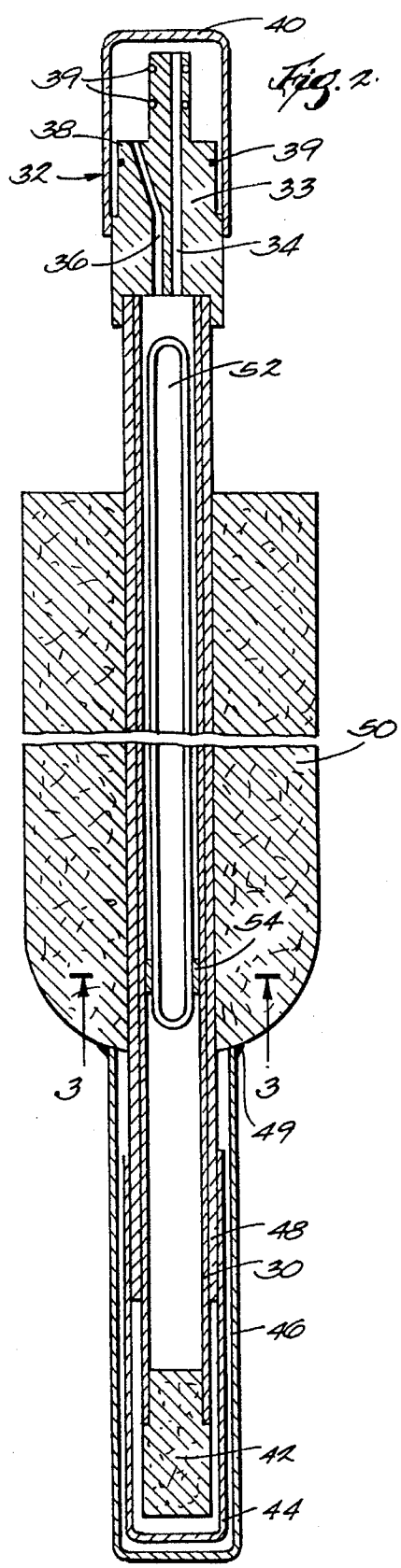
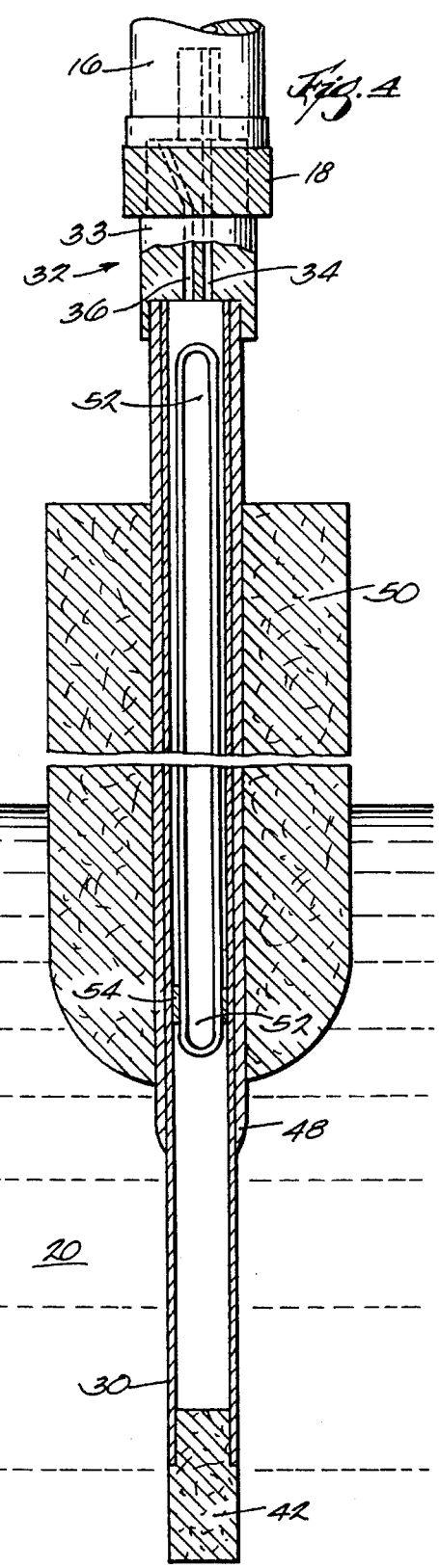

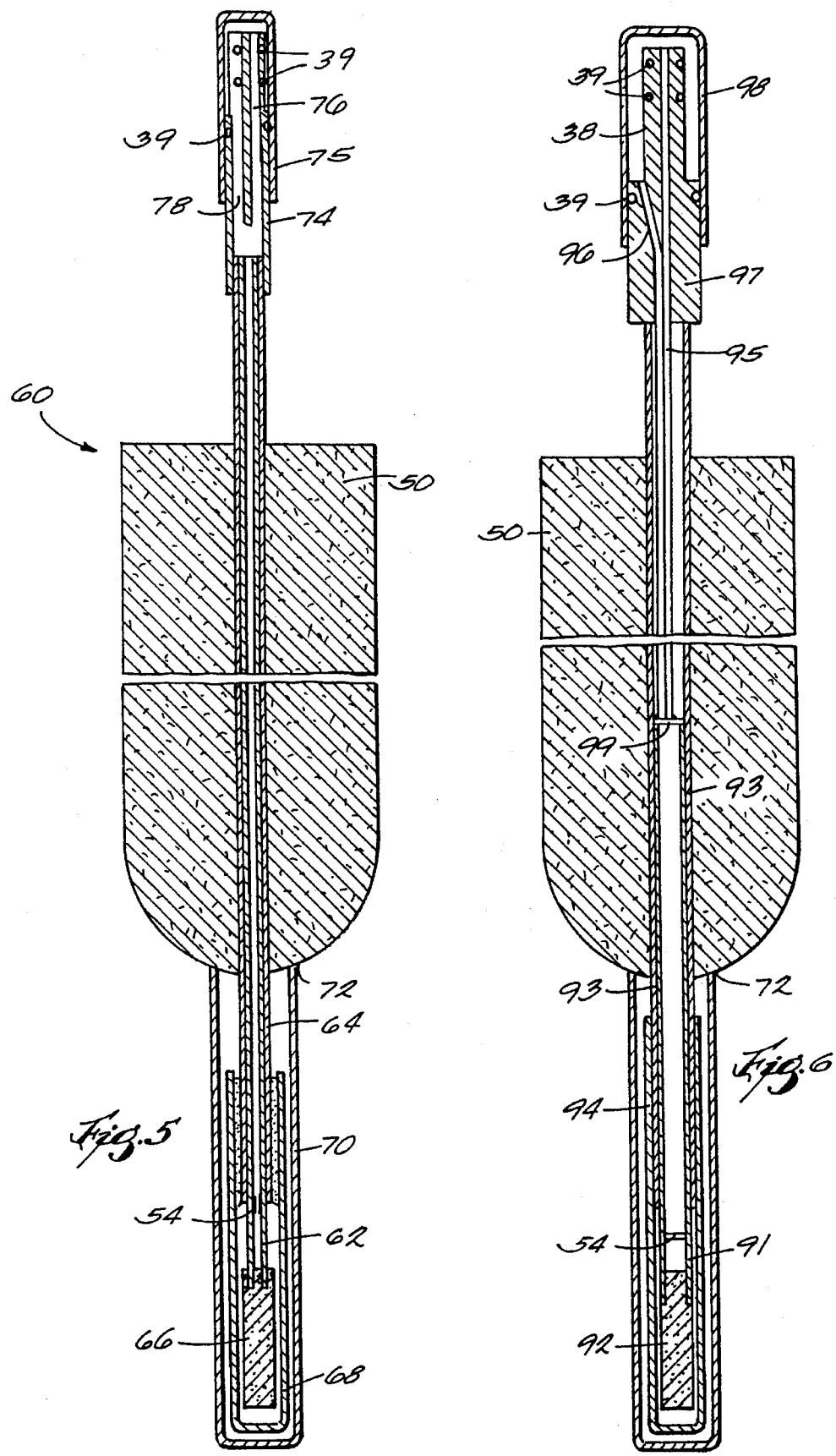

5,591,894

HYDROGEN SAMPLER FOR MOLTEN METAL AND METHOD

This is a continuation-in-part of application Ser. No. 08/500,318 filed on Jul. 10, 1995, now abandoned.

FIELD OF THE INVENTION

The invention relates to a probe for use in apparatus and methods for measurement of gas concentrations in molten metal. More particularly, the invention relates to such a probe suitable for determination of dissolved hydrogen, oxygen or nitrogen content in molten metals such as steel.

BACKGROUND OF THE INVENTION

Various devices have been developed heretofore to measure the content of dissolved gases such as hydrogen in molten metals such as molten aluminum or molten steel. An early device is described in U.S. Pat. No. 2,861,450 issued to Ransley et al. The device shown therein referred to as the Telegas device. This device included in immersion head of generally a bell-shaped configuration and entailed discharging or debouching a carrier gas into the molten metal and recapturing bubbles using the bell-shaped device. The nitrogen reached an equilibrium with the dissolved hydrogen, which thus enabled monitoring and measurement of the dissolved hydrogen content in the metal.

An improved measurement system is described in Marten et al., U.S. Pat. No. 4,907,440, assigned to Alcan International, Ltd. In that patent, a probe is disclosed whose sensor is formed from a block of gas permeable, liquid metal-impervious material such as alumina. A carrier gas is caused to flow within the block. The block enabled entrainment of dissolved gases which diffused to the interior of the block from the ambient molten metal. The device, thus, no longer required discharge of gas bubbles into the metal nor recapturing of such bubbles.

SUMMARY OF THE INVENTION

It is a principal object of the invention to provide a new and improved probe for determination of dissolved gas contents in molten metals. The invention has important application to the determination of the concentrations of hydrogen dissolved in molten steel, but can be used also to determine concentrations of other dissolved gases such as oxygen or nitrogen. The invention also has applicability to determination of dissolved gas concentrations in most other molten metals such as copper, aluminum, tin or lead.

An important aspect of the invention relates to providing of an immersion probe which is provided to a metal melter or refiner in a dry sealed condition containing a dry inert carrier gas. A related aspect entails use of this same carrier gas as a vehicle for transport through the probe for analysis of a gas whose concentration is to be determined. Another related important advantage of the invention relates to the use of such confined inert gas, eliminating entirely the necessity of using a flowing stream of the carrier gas through the sensor. In accordance with a further related aspect, the invention provides a probe wherein, unlike prior art devices, a confined, flowing carrier gas is not introduced into or caused to flow through a hot zone within the sensor, ie, at a level below that to which the probe is immersed in the molten metal.

It is a further object of the invention to provide an immersible tubular body for a probe device which provides a highly effective hydrogen and other gas impermeable seal that avoids introduction of contaminants from the sensor into the metal bath being monitored or, subsequently, into the gases contained in the inner area of the probe. In accordance with a related aspect of the invention such sealing materials are provided which are meltable or fusible in the metal bath and which uses components compatible with (or nearly identical in composition to) the specific metal being monitored. In accordance with a still further related aspect the seal is provided by an elongated tubular heat resistant glass or quartz body encased by a metallic tube. The metal tube forms part of a hermetic seal during storage or shipment. This metal tube then, itself melts when immersed and then forms a continuous seal together with the surrounding molten metal in the bath. In accordance with a yet further aspect of the invention such seal remains effective to retain gases within the probe and to seal out impurities even in the event of internal fracture of the underlying glass or quartz tube.

Briefly, the invention provides an immersion probe for determination of the concentration of a gas dissolved in molten metal which includes a probe body in the form of an elongated, preferably hermetically sealed, housing. The body has a first end adapted to be connected to a gas flow conduit located out of the hot zone, the first end being preferably sealed, until use, by a temporary sealing means. The body has a second end adapted to be immersed in molten metal, the second end is spaced from and in fluid flow communication with the first end and has a porous, gas-permeable but liquid metal-impervious plug. The second end and the plug are sealed by a molten metal-soluble cap until melted during immersion into molten metal. An inert, dry carrier gas such as nitrogen or argon may be sealed within the probe body. The probe may have a single gas connection. After immersion the probe of this embodiment is preferably purged with inert dry gas for about 15–30 seconds and then a negative pressure is drawn using a pump. Dissolved gas concentration is then determined by a connected analysis device within about one to twenty seconds after gas flow out of the probe body reaches a minimum value by virtue of the constant negative pressure thus drawn by the pump and the gas content of the metal.

In a preferred embodiment, a metal sleeve around the sealed housing, preferably of a composition fusible in and compatible with a molten metal being monitored may be used to provide a fluid impermeable seal for the probe body which seals in gases and seals out molten metals and impurities for a time sufficient to complete the desired gas analysis. The metal sleeve also serves as a support or reinforcement for the probe, especially for the quartz tube, increasing its strength needed to support the porous plug during immersion.

BRIEF DESCRIPTION OF THE DRAWINGS

FIG. 1 is a perspective view of a probe system in accordance with the invention including a fragmentary view of a metal bath;

FIG. 2 is a central cross sectional view of an immersible probe in accordance with an embodiment of the invention;

FIG. 3 is a sectional view taken along line 3—3 of FIG. 2;

FIG. 4 is a central cross sectional view of the probe shown in FIG. 2 after removal of temporary seals and connection thereof to an analysis system and immersion in a metal bath;

FIG. 5 is a central sectional view showing another embodiment of the invention;

FIG. 6 is a central cross sectional view showing yet another embodiment of the invention.

DETAILED DESCRIPTION OF PREFERRED EMBODIMENTS

Figure 7:
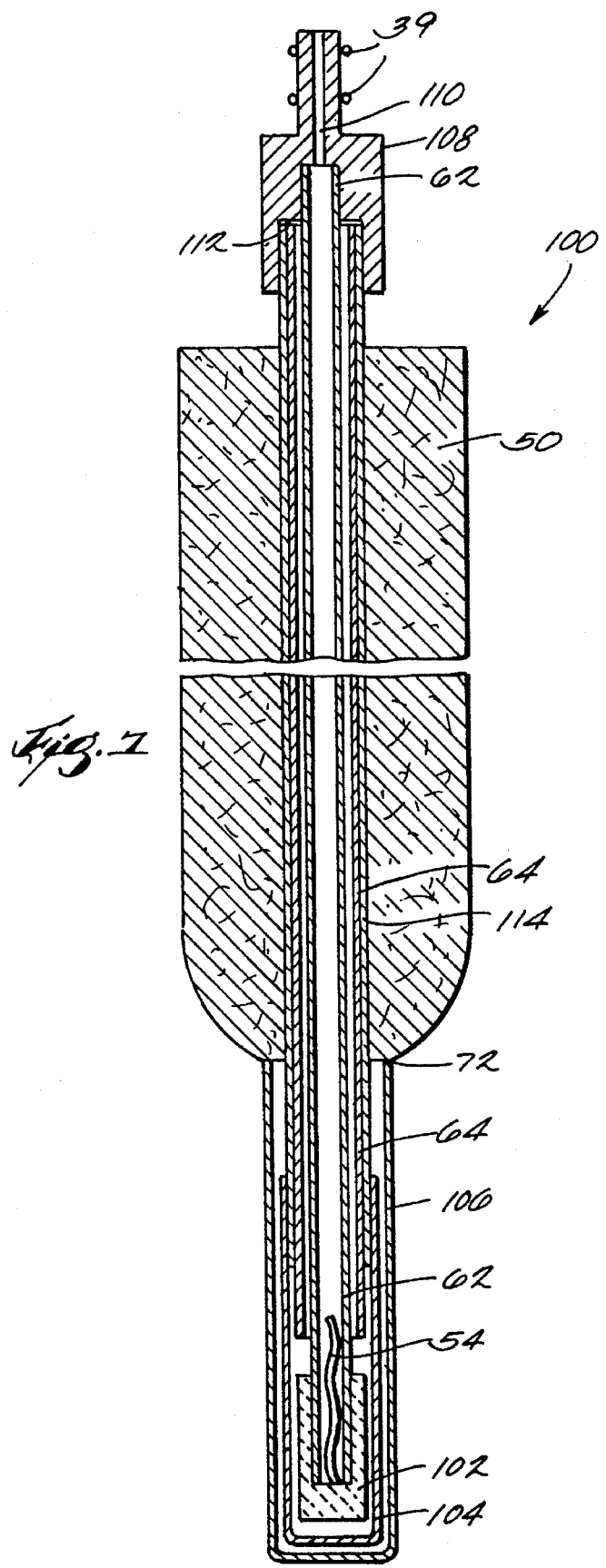
FIG. 7 is a central cross sectional view showing another embodiment of the invention.

Referring more particularly to the drawings there is seen in FIG. 1 an analysis system 10 for determining dissolved gas concentration in metals. The system 10 includes an immersible probe component 12 and a gas analysis device 14. Probe 12 is in fluid flow connection with analysis device 14 by means of tubing 16 which is preferably connected to the top end of probe 12 by means of a quick-connect coupling 18. As shown in FIG. 1 probe 12 is immersible into molten metal 20 shown in this case as being contained within a vessel 22.

Referring to FIGS. 2–4, further details of the immersible probe component 12 can be observed. As seen in FIG. 2 immersible probe component 12 is hermetically sealed prior to use.

Immersible probe 12 is formed of a tubular body portion 30 preferably cylindrical in shape. Body 30 is preferably formed of a heat resistant glass or quartz. Probe 12 includes an upper end 32 for connection to conduit 16 by means of coupling 18. Upper end portion 32 is preferably formed by a metal connector block 33 which contains channels or bores 34 and 36 for connection to corresponding fluid flow channels in conduit 16. O-ring type connection fittings 38 (including O-rings 39 of appropriate sizes) are provided for attachment of immersible probe component 12 to conduit 16 by means of coupling 18. A removable cap 40 hermetically seals the upper end of probe body 12 effectively closing and/or separating bores 34 and 36 from the atmosphere. Cap 40 is removable and is intended to be removed immediately prior to connection of immersible probe 12 to conduit 16. Bores 34 and 36 may be, for example, 1/32 inch in diameter.

The lower end of probe 12, which is intended for immersion in molten metal bath 20, includes a block 42 of gas permeable but molten metal-impervious material such as a refractory alumina or similar refractory material. The bottom end of tube 30 and porous block 42 are hermetically sealed by a molten metal fusible cap of 44 which may be formed, for example of fusible metal such as steel or aluminum. Caps 40 and 44 together with the body of tubular members 48 and 30 provide a vacuum and air tight hermetic seal within which an inert carrier gas such as nitrogen or argon is contained.

In order to avoid introducing contaminants into the molten metal bath it is preferred that the bottom end of tube 30 be fused to block 42 and that no adhesive or a minimal amount of a non-contaminating adhesive be used. A paper protective sleeve 46 is provided around sleeve 44. Sleeve 46 provides temporary protection and also as it burns quickly upon immersion of the probe 12 into molten metal it exudes gases which assist in clearing slag away from the probe 12, thus avoiding adherence of such materials to the sensor or probe 12.

A sleeve 48 of metal is provided over at least the central portion and preferably the entire length of tube 30, with the exception of the lowermost end which is sealed within fusible cap 44, as seen in FIG. 2. It is preferred that sleeve 48 be formed of a metal similar to or compatible with the metal in the bath that is being monitored. Thus, for example, if hydrogen content of steel is being determined, it is desirable that sleeve 48 be formed of steel. If gas concentrations in an aluminum bath are being determined it is preferred that sleeve 48 be formed of aluminum and if gas content of copper is being determined that the sleeve 48 be formed of copper, etc. It has been found that the presence of sleeve 48 provides an outer surface around tube 30 that melts and fuses together with the material of the metal bath thereby forming a fluid and gas impervious seal. The molten metal to solid metal seal thus formed by the molten metal around sleeve 30 has been found to be highly effective in confining gases within the probe and prevents inflow therein of impurities from the molten metal bath or the ambient atmosphere even in cases where internal failure or cracking of tube 30 occurs.

A heat protective refractory fiber sleeve or metal reinforced foundry sand sleeve 50 is provided for added protection around the central portion of probe 12. Sleeves incorporating resin binders such as urethanes or phenols can also be used. The protective sleeve 50 is adhered to cardboard sleeve 46 by means of a refractory or organic cement 49 or, alternatively secured to sleeve 48.

In order to rapidly and accurately analyze for gas content it is desirable that the interior of tube 30 be of as small a volume as practical. To this end it has been found that an insert 52, which is preferably in the form of an evacuated hollow quartz tube sealed at each of its opposite ends, is effective in reducing the interior volume of tube 30, thereby providing a speedy response time for the probe 12. Other volume reducing devices such as a solid rod of quartz or other inert material could, of course, be substituted. It has been found that volume reducing tube 52 does not have to be adhered to the inside of tube 30 but can simply be placed therein. Thus in the event that tube 52 were to slide to the bottom of the interior of tube 30 such movement would be of no practical consequence.

Also contained within hollow tube 30 is zirconium foil 54, which, as seen in FIG. 3, does not block gas flow through the tube 30. The zirconium foil acts as an effective purging device for removal of oxygen from the gases diffusing through the inside of tube 30.

It should be noted that metal connector block 33 can be attached to the exterior of metal sleeve 48 by brazing, gas impervious ceramic cements or other similar bonding techniques. It will be noted that, the even when probe 12 is immersed into molten metal bath 20, this seal remains in the cold zone, ie., in a well protected area or, above the level to which the probe is immersed. Therefore impurities which could be released from sealing materials at high temperatures are avoided.

The embodiments of FIGS. 5 and 6 are of a configuration which volume of the probe body is reduced by use of a smaller diameter tubular body.

Referring to FIG. 5 there is seen a modified probe 60 which includes quartz or heat resistant gas impervious glass tube 62 provided with a concentric enclosing metal tube 64. In one preferred embodiment tube 62 has an inside diameter of 2 mm. and a wall thickness of 2 mm. The bottom end of tube 62 is connected by means of physical insertion into a block 66 of gas permeable, molten metal-impervious refractory material. A temporary molten metal-fusible cap 68 forms a temporary seal, providing hermetic sealing for the lower end of probe 60. As in the case of the earlier embodiment a temporary protective cap 70 of cardboard or the like is also provided. The cap 70 is sealed, for example by organic or refractory cement 72 to protective body 50 or to the outside of cap 68. A metal connector block 74 is connected by brazing, refractory cement or otherwise to metal tube 64 and quartz tube 62 to hermetically seal the upper end of probe 60. A removable cap 75 hermetically seals the upper end of probe 60, including inlet and outlet channels 76 and 78 until probe 60 is ready for use.

In the further modified version shown in FIG. 6 probe 90 includes a quartz tubular body 91 connected to a porous molten metal impervious, gas permeable block 92. Similar to the components of the earlier described embodiments, an outlet conduit 95 is connected through metal connector block 97 to conduit 16 by means of a quick connect coupling 18 similar to that previously described. A temporary hermetic cap 98 is provided over the top end of probe 90 as in the case of the earlier embodiments. A second conduit 96 is provided as an inlet to allow entry of gas into the interior of tube 91 during immersion, as needed, to avoid drawing of a negative pressure within the probe. Conduits 95 and 96 are preferably affixed by brazing to a disc 99 which is attached by tack welding and sealed by gas impervious refractory cement to and which closes the upper ends of metallic tube 93 and tubular body 91.

In use it has been found that the probes of the present invention, all containing a sealed-in carrier gas are effective in diffusionally transmitting therethrough dissolved hydrogen contained in a metal bath 20 in that the hydrogen content within the carrier gas contained within the probe reaches an equilibrium quickly, generally within 30 to 90 seconds after immersion and melting of lower protective caps 44, 68 or 94. Thus the introduction of a separate flow of carrier gas through the probe as required by the prior art is not necessary. Accurate hydrogen content measurements can thus be conducted in a very short time. Analysis instrument 14 can be any suitable available gas analysis device, for example of the type shown in the Martin et al, 440 patent referred to above, the disclosure of which is incorporated herein by reference. Other suitable gas analysis equipment can, of course be substituted as desired.

Referring to the embodiment of FIG. 7 there is seen a device 100 which is provided with only a single gas flow opening 110 for connection to conduits leading to an analysis device 14. A porous block 102 similar to that used in the previous embodiments is connected to the lower end of a hollow quartz tube 62 within which a purging amount of zirconium foil 54 is located. As in the case of the previous embodiments a molten metal fusible temporary cap 104 is preferably used to hermetically seal the lower end of the probe. A temporary cardboard cap 106 is also positioned around the lower end and connected to protective body 50 by means of an adhesive or cement 72.

Also as in the case of the earlier embodiments a quartz tube 64 and a metal tube 114 are positioned concentrically around tube 62. The upper ends of the assembly are connected to a connecting block 108 which has a single opening 110. The assembly of tubes is hermetically sealed to block 108 at the abutting connection point 112.

Probe 100 is preferably used by immersion into molten metal after connection to a conduit leading to an analysis device 14. During burning away of cap 106 and fusion of cap 104 in the molten metal, a brief purge cycle is preferably utilized wherein dry inert gas is introduced through opening 110 for approximately 15–30 seconds. Thereafter the purging flow is discontinued and negative pressure is formed within tube 62 through use of a vacuum pump. Negative pressure of approximately 15 mm Hg is generally a suitable amount of negative pressure. After flow to the vacuum pump reaches a minimum, the hydrogen or other dissolved gas content is allowed to reach equilibrium and an accurate reading of the concentration in the metal is determined within about 1 to 20 seconds after ceasing of pumping of the purging gas.

Sensing device 14 may preferably be a katharometer. Since such devices are known to the art it will not be described in detail herein. It will be understood that any other analysis device for determination of gas concentrations can be used instead. Other devices which may be substituted include gas chromatograph, thermoconductivity cells or mass spectrometer.

While various preferred embodiments of the invention have been shown for purposes of illustration it will be understood that the invention should not be limited thereto but include reasonable equivalent structures to those set forth in the appended claims.

What is claimed is:

1. An immersion probe for determination of the concentration of a gas dissolved in molten metal by immersion of said probe in said metal comprising, a heat resistant probe body in the form of a housing having an elongated configuration, said body being formed of a non-metallic, solid, gas and molten metal impervious material encased in a tube of metal;

said body having a first end adapted to be connected to a gas conduit;

said body having a second end adapted to be immersed in molten metal, said second end being spaced away from, but in fluid flow communication with, said first end and having a gas-permeable, liquid metal-impervious plug, said second end and said plug being sealed by a molten metal-soluble cap.

2. A probe according to claim 1 wherein said probe body is sealed and filled with dry inert gas.

3. A probe according to claim 1 wherein said elongated body comprises a quartz tube.

4. A probe according to claim 3 adapted to measure gas content within a selected metal and wherein the exterior of said quartz tube is surfaced by a layer of said selected metal.

5. A probe according to claim 1 wherein said first end comprises a single gas flow opening.

6. A probe according to claim 5 wherein a connector block is attached to said first end, said opening extending centrally through said block.

7. A probe according to claim 6 wherein said plug comprises a gas permeable refractory material.

8. A probe according to claim 7 wherein said plug comprises alumina.

9. A probe according to claim 1 wherein said first end of said probe is connected to a gas analysis device.

10. A probe according to claim 1 in which said first end comprises a connector block which has a single gas flow opening therethrough and which is hermetically sealed to the upper end of said probe body.

11. A probe according to claim 1 wherein a portion of said elongated body between the first and second ends is provided with a protective layer of heat resistant material.

12. A probe according to claim 1 wherein a temporary protective combustible layer is provided over said second end.

13. A method for determining hydrogen content in molten metal comprising providing a probe as defined in claim 1 said probe being connected by a gas flow conduit to a hydrogen analysis device;

immersing said probe in said molten metal;

purging said probe with an inert gas;

drawing a negative pressure within the body of said probe until gas flow therefrom reaches equilibrium; and, using said analysis device to determine the content of hydrogen gas dissolved in said metal.

14. A method according to claim 13 wherein said gas content is determined approximately one to twenty seconds after said gas flow reaches equilibrium.

15. A method according to claim 14, wherein said dry inert gas comprises nitrogen.

16. A method according to claim 14 wherein said body comprises a cylindrical tube or assembly of cylindrical tube having an inner opening with a diameter of about 2 mm.

17. An immersion probe for determination of the concentration of a gas dissolved in molten metal by immersion of said probe in said metal comprising, a probe body in the form of a hermetically sealed housing having an elongated configuration, said body being formed of a gas and liquid metal impervious material of sufficient resistance to withstand immersion in molten metal;

said body having a first end adapted to be connected to a gas inlet and a gas outlet, said first end being hermetically sealed by a temporary sealing means;

said body having a second end adapted to be immersed in molten metal, said second end being in fluid flow communication with said first end and having a gas-permeable, liquid metal-impervious plug, said second end and said plug being hermetically sealed by a molten metal-soluble cap; and, an inert, dry carrier gas sealed within said probe body.

18. A probe according to claim 17 wherein said inert gas is nitrogen.

19. A probe according to claim 17 wherein said elongated body comprises a quartz tube.

20. A probe according to claim 17 wherein said elongated body comprises an elongated volume reducing means located within said body.

21. A probe according to claim 20 wherein said elongated volume reducing means comprises an evacuated hollow quartz tube sealed at each of its opposite ends.

22. A probe according to claim 21 wherein said plug comprises a porous refractory material.

23. A probe according to claim 22 wherein said plug comprises alumina.

24. A probe according to claim 17 wherein an inlet and an outlet at the first end of said probe are connected to a gas analysis device.

25. A probe according to claim 17 adapted to measure gas content within a selected metal and wherein the exterior of said quartz tube is surfaced by a layer of said selected metal.

26. A probe according to claim 17 in which said first end comprises a connector block which is hermetically sealed to the upper end of said probe body, said end being adapted to remain above the level of the molten metal during immersion.

27. A probe according to claim 17 wherein a portion of said elongated body between the first and second ends is provided with a protective layer of heat resistant material.

28. A probe according to claim 17 wherein a temporary protective combustible layer is provided over said second end.

29. A probe system comprising a hydrogen analysis device connectable in fluid flow communication with a temporarily hermetically sealed immersible probe component containing an inert carrier gas, said probe component having an inlet and an outlet at a first end connectable to said analysis device, said immersible component comprising a heat resistant tube sealed prior to use at said first end by a removable cap, and having a fluid flow passage extending through the length of said tube, a second end of said tube being closed by means of a gas permeable, liquid metal impervious block of heat resistant material, said second end being temporarily sealed by a cap fusible in said molten metal, whereby hydrogen gas dissolved in said metal is enabled to flow into the interior of said immersible probe and equilibrate with said carrier gas to said analysis device after immersion of said probe component in a molten metal bath.

30. An immersible probe for determination of the concentration of a gas dissolved in molten metal by immersion of the probe in said metal comprising, a tubular heat resistant glass or quartz probe body adapted to receive gases contained in said molten metal for analysis;

said body having a first end adapted to be connected to a gas outlet, said first end being hermetically sealed by a temporary sealing means;

said body having a second end adapted to be immersed in molten metal, said second end being in fluid flow communication with said first end and having a gas-permeable, liquid metal-impervious plug, said second end and said plug being hermetically sealed by a molten metal-soluble cap;

an inert, dry carrier gas sealed within said probe body a tubular metallic sleeve surrounding at least a portion of the length of said tubular body, said sleeve being adapted to melt after immersion of said probe in said molten metal thereby forming a substantially gas impervious envelope of liquid and solid metal around said tubular body.

31. A probe according to claim 30 provided for analysis of hydrogen concentration in molten steel, wherein said dry inert gas comprises nitrogen and said metallic sleeve comprises steel.

32. A probe according to claim 30 wherein said body comprises a cylindrical tube having an inner diameter of about 2 mm.

33. A probe according to claim 30 wherein said molten metal soluble cap is sealed to said tubular metal sleeve.

34. A probe according to claim 29 wherein said second end is enclosed by a paper cap, sealing cements which are combustible in molten metal and produce gases which are located on the lower end of said probe to carry slag and impurities away from said probe.

35. A probe according to claim 30 wherein all heat sensitive gas seals other than said molten metal-soluble cap are positioned at the upper end of said probe, which remains cool during immersion, whereby said seals are protected from impurity releasing heat.

\* \* \* \* \*